(12) United States Patent
Duffy

(10) Patent No.: US 8,439,840 B1
(45) Date of Patent: May 14, 2013

(54) ULTRASOUND IMAGING SYSTEM AND METHOD WITH AUTOMATIC ADJUSTMENT AND/OR MULTIPLE SAMPLE VOLUMES

(75) Inventor: Thomas M. Duffy, Snohomish, WA (US)

(73) Assignee: SonoSite, Inc., Bothell, WA (US)

( * ) Notice: Subject to any disclaimer, the term of this patent is extended or adjusted under 35 U.S.C. 154(b) by 299 days.

(21) Appl. No.: 12/773,665

(22) Filed: May 4, 2010

(51) Int. Cl.
*A61B 8/00* (2006.01)

(52) U.S. Cl.
USPC ........... 600/443; 600/437; 600/440; 600/446; 600/455; 600/459

(58) Field of Classification Search ............... 600/437, 600/440, 443, 446, 455, 459
See application file for complete search history.

(56) References Cited

U.S. PATENT DOCUMENTS

| | | | |
|---|---|---|---|
| 5,409,010 A * | 4/1995 | Beach et al. ................... | 600/455 |
| 5,429,137 A * | 7/1995 | Phelps et al. ................... | 600/455 |
| 5,817,024 A | 10/1998 | Ogle et al. | |
| 5,893,363 A | 4/1999 | Little et al. | |
| 6,508,768 B1 * | 1/2003 | Hall et al. ..................... | 600/443 |
| 7,604,596 B2 | 10/2009 | Hwang et al. | |
| 2006/0116578 A1 * | 6/2006 | Grunwald et al. ............ | 600/440 |
| 2007/0239001 A1 * | 10/2007 | Mehi et al. .................... | 600/437 |

\* cited by examiner

*Primary Examiner* — Tse Chen
*Assistant Examiner* — Baisakhi Roy

(57) ABSTRACT

Adjustment of operation of an ultrasound imaging system may be based at least in part on one or more characteristics represented in ultrasound return signals from two or more sample volumes. Adjustment may include adjusting a principal sample volume location or selecting a new principal sample volume. For example, a location of a principal sample volume may be adjusted or new principal sample volume selected so as to remain focused on an identified region of interest or to maintain the principal sample volume relative to some structure or reference. The principal sample volume may be maintained in the center or along a centerline of an artery or other structure, as the transducer array is moved along the artery or structure.

25 Claims, 9 Drawing Sheets

ULTRASOUND IMAGING SYSTEM AND METHOD WITH AUTOMATIC ADJUSTMENT AND/OR MULTIPLE SAMPLE VOLUMES

BACKGROUND

1. Technical Field

This application relates to ultrasound imaging systems, for instance medical diagnostic ultrasound imaging systems and, in particular, to the use of information contained in ultrasound return signals to operate the ultrasound imaging system.

2. Description of the Related Art

Ultrasound imaging systems employ transducer arrays to produce and transmit ultrasound pressure waves into an object such as a body, tissue or other material. The transducer arrays also receive ultrasound return or echo signals and produce analog transducer element voltage signals which are induced at the transducer array by the received ultrasound return or echo signals.

Many ultrasound imaging systems are capable of operating in various modes for sampling, processing and/or presenting ultrasound information in a variety of useful representations. For example, ultrasound systems may employ A-, B-, M-, Doppler, energy, power, Doppler amplitude or color angio modes. Some ultrasound systems are capable of concurrently displaying information in more than one type of representation.

A region in three-dimensional space from which data is collected is commonly referred to as a sample volume. The sample volume typically has a width determined by the lateral margins of the ultrasound beam and an axial depth along the ultrasound beam determined by a duration of the transmitted ultrasound pulse and a duration of a sample gate implemented by the circuitry of the ultrasound imaging system.

It is often desirable or even necessary to sample or image a desired location (e.g., three-dimensional location, including axial depth) in a material. For instance, medical imaging typically involves capturing a sample or image of a volume at a desired location in a body or anatomical structure (e.g., bodily organ). In some applications, a sonographer or clinician may locate or place a sample volume with reference to a two-dimensional image (e.g., B-mode image), then switch the ultrasound imaging system into "Doppler" mode to see the "Doppler" waveform.

However, it can be difficult to maintain the sample volume in a desired location. Such may be difficult when there is no or relatively little relative movement between the transducer array and the desired location. Such may be even more difficult when there is relative movement between the transducer array and the desired location, for instance where the transducer array is translated along a tissue or structure such as along an artery. If the ultrasound imaging system has "triple" mode capability or an Echo/Doppler mode, a sonographer or clinician may use a reference to aid in manually maintaining a sample volume in a desired or correct location. However, such may adversely take away acquisition time form Doppler firings, which reduces the ability to view high flow rates.

New approaches that facilitate maintaining a sample volume at desired locations while allowing relatively high pulse repetition frequency (PRF) are desirable.

BRIEF SUMMARY

Systems and methods described herein adjust operation of an ultrasound imaging system based at least in part on one or more characteristics represented in ultrasound return signals from two or more sample volumes. Such may maintain a sample volume focused at a desired location or region of interest, for example centered with respect to some anatomical structure such as an artery. Such may facilitate ultrasound imaging when there is no or little movement of the transducer relative to the anatomical structure or when there is significant relative movement therebetween.

Such may employ multiple sample volumes. For example, one sample volume may be referred to as a principal sample volume. Other volumes around or proximate the principal sample volume may be sampled as well. The other volumes may be referred to as additional sample volumes to distinguish from the principal sample volume. The additional sample volumes may be axially and/or laterally disposed from the principal sample volume. While the principal sample volume may be locus or center of all sample volumes, such is not necessary.

The principal and additional sample volumes may be evaluated from time-to-time to determine which of the sample volumes most closely corresponds or correlates with a desired location. The sample volume which most closely corresponds or correlates with the desired location may become the next sample volume. The additional sample volumes may be similarly updated. Such may be preformed automatically be the ultrasound imaging system, for example without operator or user evaluation, selection or other intervention. Thus, for example, the system and methods may adjust a principal sample volume location or select a new principal sample volume. For example, a location of a principal sample volume may be adjusted or new principal sample volume selected so as to remain focused on an identified region of interest. Also for example, a location of a principal sample volume may be adjusted or a new principal sample volume selected so as to maintain the principal sample volume relative to some anatomical structure or some reference. For instance, the principal sample volume may be maintained in the center or along a centerline of an artery, as the transducer array is moved along the artery.

A method of operating an ultrasound imaging system may be summarized as including generating a first number of ultrasound pressure waves; receiving a first number of ultrasound return signals from a principal sample volume and at least one additional sample volume that have at least respective portions thereof that are at least one of axially displaced or laterally displaced with respect to one another in response to the first number of ultrasound pressure waves; and adjusting by a control circuit at least one operational parameter of the ultrasound imaging system based at least in part on at least one characteristic represented in the received first number of ultrasound return signals. The adjusting may be automatic, without intervention of an operator or user.

Adjusting by a control circuit at least one operational parameter of the ultrasound imaging system based at least in part on at least one characteristic represented in the received ultrasound return signals may include selecting a new principal sample volume to be sampled; and selecting a number of additional sample volumes to be sampled that have at least respective portions thereof that are at least one of axially displaced or laterally displaced with respect to the new principal sample volume. Adjusting by a control circuit at least one operational parameter of the ultrasound imaging system based at least in part on at least one characteristic represented in the received ultrasound return signals may include generating a second number of ultrasound pressure waves directed to the new principal sample volume and at least one of the additional sample volumes that have at least respective portions thereof that are at least one of axially displaced or laterally displaced with respect to the current principal sample volume.

Adjusting by a control circuit at least one operational parameter of the ultrasound imaging system based at least in part on at least one characteristic represented in the received ultrasound return signals may include selecting a new principal sample volume to be sampled; and selecting at least two additional sample volumes to be sampled that have at least respective portions thereof that are laterally opposed to one another across the new principal sample volume. Selecting a new principal sample volume may include selecting one of the principal sample volume or the at least one additional sample volume as the new principal sample volume.

Adjusting by a control circuit at least one operational parameter of the ultrasound imaging system based at least in part on at least one characteristic represented in the received ultrasound return signals may include selecting one of the principal sample volume or the at least one additional sample volume as a new principal sample volume to be sampled; and selecting at least two additional sample volumes to be sampled that have at least respective portions thereof that are axially opposed to one another across the new principal sample volume.

The method of operating an ultrasound imaging system may further include beam forming to sample a new principal sample volume; beam forming to sample at least two additional sample volumes that have at least respective portions thereof that are axially opposed to one another across the new principal sample volume; and beam forming to sample at least two additional sample volumes that have at least respective portions thereof that are laterally opposed to one another across the new principal sample volume.

Generating a first number of ultrasound pressure waves may include transmit beam forming to transmit at least one ultrasound pressure wave along an initial principal axial ray; transmit beam forming to transmit at least one ultrasound pressure wave along an initial first lateral axial ray laterally displaced from the initial principal axial ray; and transmit beam forming to transmit at least one ultrasound pressure wave along an initial second lateral axial ray laterally displaced from the initial principal axial ray and the initial first lateral axial ray. The method of generating a first number of ultrasound pressure waves may further include transmit beam forming to transmit at least one ultrasound pressure wave along a new principal axial ray; transmit beam forming to transmit at least one ultrasound pressure wave along a new first lateral axial ray laterally displaced from the new principal axial ray; and transmit beam forming to transmit at least one ultrasound pressure wave along a new second lateral axial ray laterally displaced from the new principal axial ray and the new first lateral axial ray. The method of generating a first number of ultrasound pressure waves may further include transmit beam forming to transmit at least one ultrasound pressure wave along a new principal axial ray different from the initial principal axial array; transmit beam forming to transmit at least one ultrasound pressure wave along a new first lateral axial ray laterally displaced from the new principal axial ray; and transmit beam forming to transmit at least one ultrasound pressure wave along a new second lateral axial ray laterally displaced from the new principal axial ray and the new first lateral axial ray.

Generating a first number of ultrasound pressure waves may include transmit beam forming to transmit the ultrasound pressure waves along at least three axial rays, the three axial rays laterally spaced from one another.

Receiving a first number of ultrasound return signals from a principal sample volume and at least one additional sample volume may include receive beam forming to receive ultrasound return signals in response to the at least one ultrasound pressure wave transmitted along the initial principal axial ray; receive beam forming to receive ultrasound return signals in response to the at least one ultrasound pressure wave transmitted along the initial first lateral axial ray; and receive beam forming to receive ultrasound return signals in response to the at least one ultrasound pressure wave along the initial second lateral axial ray.

The method of operating an ultrasound imaging system may further include evaluating the at least one characteristic represented in the received ultrasound return signals upon which evaluation the adjusting at least one operational parameter of the ultrasound imaging system is based.

Evaluating the at least one characteristic represented in the received ultrasound return signals may include evaluating at least one value indicative of at least one of a power, a variance, a velocity, or a set of echo data. Adjusting by a control circuit at least one operational parameter of the ultrasound imaging system based at least in part on at least one characteristic represented in the received ultrasound return signals may include selecting a new principal sample volume to at least partially coincide with a region of interest in an object being imaged; and selecting a number of additional sample volumes to be sampled that have at least respective portions thereof that are at least one of axially displaced or laterally displaced with respect to the new principal sample volume. Adjusting by a control circuit at least one operational parameter of the ultrasound imaging system based at least in part on at least one characteristic represented in the received ultrasound return signals may include selecting a new principal sample volume to be centered with respect to at least one structure of an object being imaged; and selecting a number of additional sample volumes to be sampled that have at least respective portions thereof that are at least one of axially displaced or laterally displaced with respect to the new principal sample volume.

An ultrasound imaging system may be summarized as including at least one transducer array; at least one control system including a number of beam formers communicatively coupled to the at least one transducer array and at least one controller communicatively coupled to the beam formers, the control system configured to: generate a first number of ultrasound pressure waves by the at least one transducer array; receive a first number of ultrasound return signals via the at least one transducer array, the first number of ultrasound return signals received from a principal sample volume and at least one additional sample volume that have at least respective portions thereof that are at least one of axially displaced or laterally displaced with respect to one another in response to the first number of ultrasound pressure waves; and adjust at least one operational parameter of the ultrasound imaging system based at least in part on at least one characteristic represented in the received first number of ultrasound return signals; and at least one display communicatively coupled to the control system to receive at least image data therefrom for display of images on the display. Adjustment may be automatic, without the intervention of an operator or user.

To adjust the at least one operational parameter of the ultrasound imaging system based at least in part on at least one characteristic represented in the received ultrasound return signals, the control circuit may select a new principal sample volume to be sampled; and select a number of additional sample volumes to be sampled that have at least respective portions thereof that are at least one of axially displaced or laterally displaced with respect to the new principal sample volume.

The control circuit may be further configured to: generate a second number of ultrasound pressure waves directed to the new principal sample volume and at least one of the additional sample volumes that have at least respective portions thereof that are at least one of axially displaced or laterally displaced with respect to the new principal sample volume.

To adjust the at least one operational parameter of the ultrasound imaging system based at least in part on at least one characteristic represented in the received ultrasound return signals, the control circuit may select a new principal sample volume to be sampled; and select at least two additional sample volumes to be sampled that have at least respective portions thereof that are laterally opposed to one another across the new principal sample volume.

To adjust at least one operational parameter of the ultrasound imaging system based at least in part on at least one characteristic represented in the received ultrasound return signals, the control circuit may select one of the principal sample volume or the at least one additional sample volume as a new principal sample volume; and select at least two additional sample volumes to be sampled that have at least respective portions thereof that are axially opposed to one another across the new principal sample volume.

To generate a first number of ultrasound pressure waves the control circuit may generate at least one ultrasound pressure wave along an initial principal axial ray; generate at least one ultrasound pressure wave along an initial first lateral axial ray laterally displaced from the initial principal axial ray; and generate at least one ultrasound pressure wave along an initial second lateral axial ray laterally displaced from the initial principal axial ray and the initial first lateral axial ray. The control circuit may be further configured to: generate at least one ultrasound pressure wave along a new principal axial ray; generate at least one ultrasound pressure wave along a new first lateral axial ray laterally displaced from the new principal axial ray; and generate at least one ultrasound pressure wave along a new second lateral axial ray laterally displaced from the new principal axial ray and the new first lateral axial. The control circuit may be further configured to: generate at least one ultrasound pressure wave along a new principal axial ray different from the initial principal axial array; generate at least one ultrasound pressure wave along a new first lateral axial ray laterally displaced from the new principal axial ray; and generate at least one ultrasound pressure wave along a new second lateral axial ray laterally displaced from the new principal axial ray and the new first lateral axial ray.

The control circuit may be further configured to: evaluate at least one value indicative of at least one of a power, a variance, a velocity, or echo data as the at least one characteristic represented in the received ultrasound return signals. To adjust at least one operational parameter of the ultrasound imaging system based at least in part on at least one characteristic represented in the received ultrasound return signals, the control circuit may select a new principal sample volume to be sampled to at least partially coincide with a region of interest in an object being imaged; and select a number of additional sample volumes to be sampled that have at least respective portions thereof that are at least one of axially displaced or laterally displaced with respect to the new principal sample volume. To adjust at least one operational parameter of the ultrasound imaging system based at least in part on at least one characteristic represented in the received ultrasound return signals, the control circuit may select a new principal sample volume to be sampled to be centered with respect to at least one structure of an object being imaged; and select a number of additional sample volumes to be sampled that have at least respective portions thereof that are at least one of axially displaced or laterally displaced with respect to the new principal sample volume.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1:
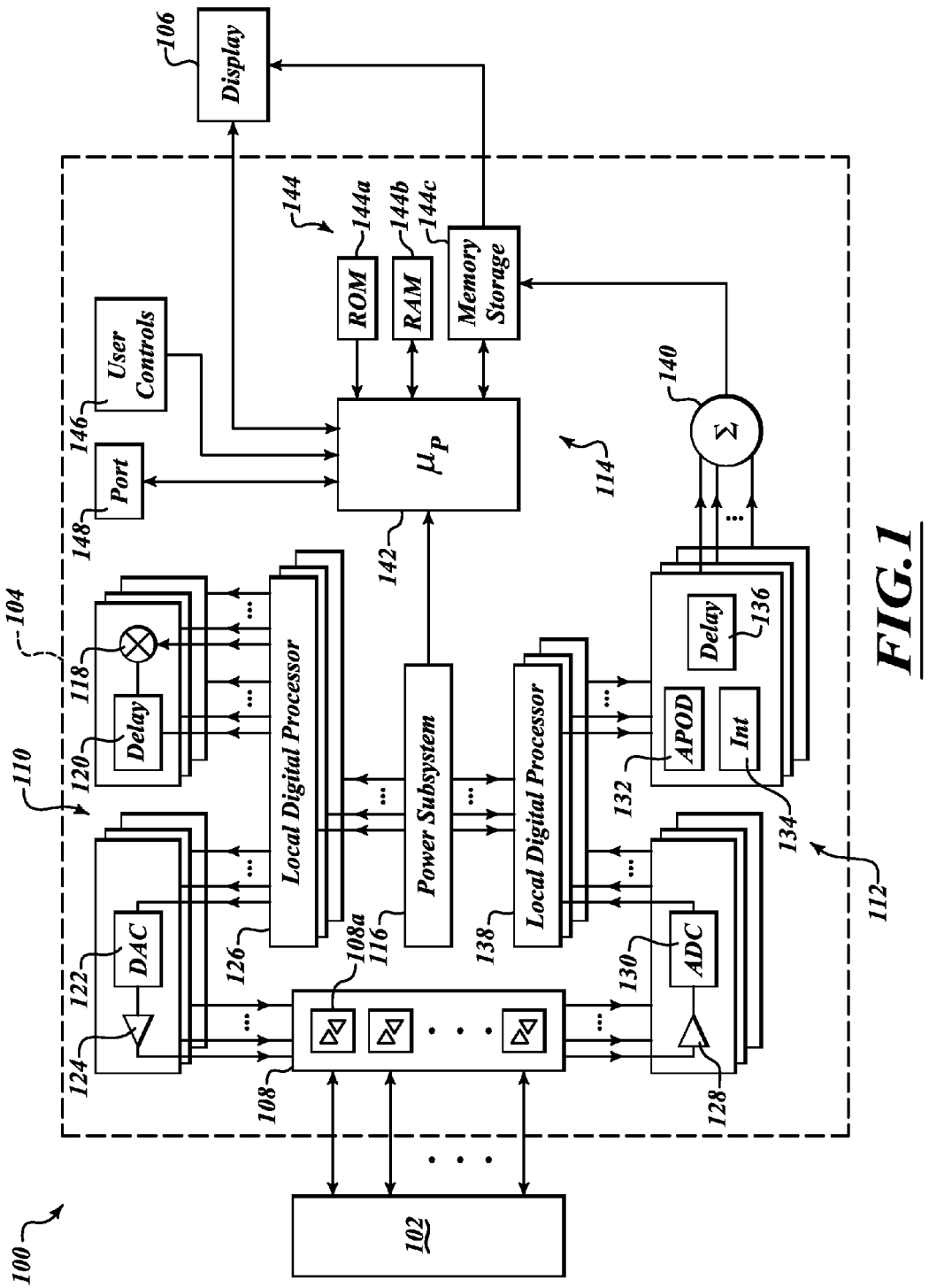
FIG. 1 is a schematic diagram of an ultrasound imaging system according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with ultrasound imaging systems, microprocessors, micro-controllers, application specific integrated circuits, transducers and displays have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

Systems and methods described herein adjust operation of an ultrasound imaging system based at least in part on one or more characteristics represented in ultrasound return signals from two or more sample volumes. The adjustment may be automatic, without evaluation, selection or other intervention or action of an human operator or user beyond standard operations of selecting a mode and scanning.

As discussed in the Brief Summary section, the systems and methods described herein may maintain a sample volume focused at a desired location or region of interest, for example centered with respect to some anatomical structure.

During any given period, multiple sample volumes may be sampled. One of the sample volumes may be referred to as a principal sample volume, while others sample volumes axially and/or laterally disposed from the principal sample volume may be referred to as additional sample volumes, to distinguish such from the principal sample volume. For axially spaced sample volumes (i.e., at different depths) the same received ultrasound return signals may be filtered for different sample volume depths, adding little or acceptable acquisition time. For laterally spaced sample volumes may employ multiline acquisition techniques that employ additional receive beamformers to acquire sample volumes laterally spaced from the axis or ray of the principal sample volume.

From time-to-time the principal and additional sample volumes may be evaluated to determine which of the sample volumes most closely corresponds or correlates with a desired location or region of interest. The sample volume which most closely corresponds or correlates with the desired location may become the next sample volume and the additional sample volumes may be updated accordingly. Such may assist in keeping or maintaining the ultrasound sampling focused at a desired location, even when there is relative movement between the transducer array and the material being imaged or sampled. The evaluation may be based on a variety of characteristics or criteria, for example anatomical structure as represented in echo data, or one or more values indicative of power, variance, and/or velocity.

Figure 8:
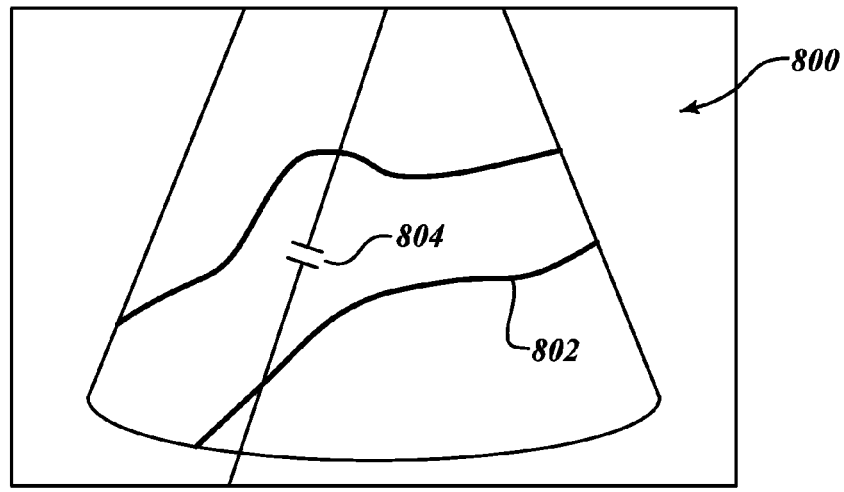
FIG. 8 is an ultrasound image showing a structure and a region of interest according to one illustrated embodiment.
Figure 9:
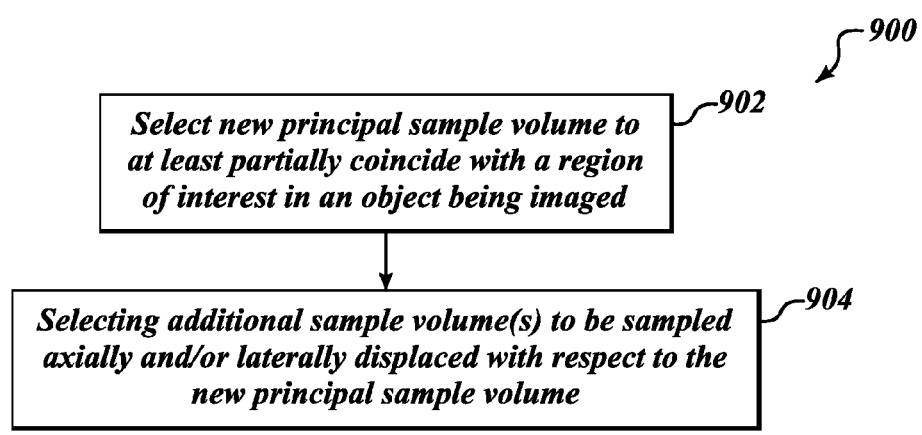
FIG. 9 is a high level flow diagram of a method of operating an ultrasound imaging system according to one illustrated embodiment, including selecting a new principal sample volume with reference to a region of interest, in accordance with the method of FIG. 5.
Figure 10:
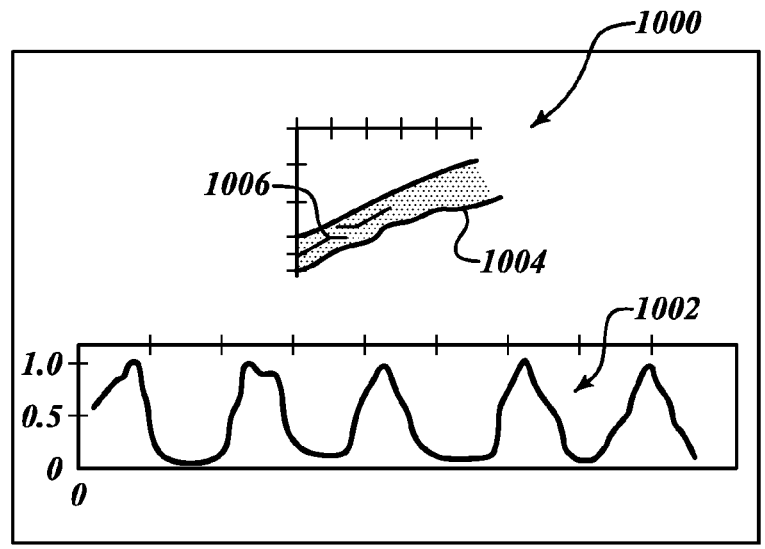
FIG. 10 is an ultrasound image showing a structure and a sample volume as well as a spectral Doppler trace according to one illustrated embodiment.
Figure 11:
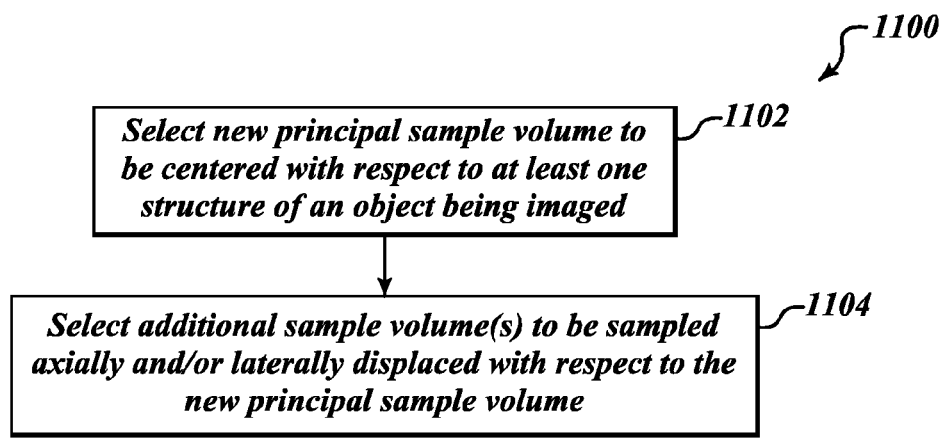
FIG. 11 is a high level flow diagram of a method of operating an ultrasound imaging system according to one illustrated embodiment, including selecting a new principal sample volume with reference to at least one structure of an object being imaged, in accordance with the method of FIG. 5.

Operation may, for example, include adjusting a principal sample volume location or selecting a new principal sample volume, as illustrated in FIGS. 2-7. For example, a location of a principal sample volume may be adjusted or new principal sample volume selected so as to remain focused on an identified region of interest, such as illustrated in FIGS. 8 and 9. Also for example, a location of principal sample volume may be adjusted or a new principal sample volume selected so as to maintain the principal sample volume relative to some structure. For instance, the principal sample volume may be maintained in the center or an artery, as the transducer array is moved along the artery, such as illustrated in FIGS. 10 and 11. Hence, a number of sample volumes may be acquired around a reference or region or interest, and which sample volume is displayed may be adjusted based on criteria (e.g., power, variance, velocity, echo) for a specific mode.

FIG. 1 shows an ultrasound imaging system 100 according to one illustrated embodiment.

The ultrasound imaging system 100 includes a transducer array 102, a control system 104 and a display 106. The transducer array 102, control system 104 and display 106 are coupled by one or more communications paths or buses. For example, the transducer array 102, control system 104 and display 106 may be coupled by one or more data buses, instructions buses, and/or power buses. Such paths or buses may take a variety of forms, including electrically conductive paths such as wires or electrical cables, or optical paths such as fiber optical cable.

The transducer array 102 produces and transmits ultrasound waves (e.g., pulse and/or continuous) into an object, such as a body, tissue or other material. The transducer array 102 also receives ultrasound return signals (e.g., echoes) and produces corresponding analog return signals (e.g., transducer element voltage signals) which are induced at the transducer array by the received ultrasound return signals. The transducer array 102 may take the form of a solid state device that allows for electronic control capabilities, variable aperture, and which provides excellent image performance and high reliability. The transducer array 102 may take the form of either a flat linear array or a curved linear array of elements. A curved linear array may provide a broad sector scanning field. The geometric curvature of a curved linear array may advantageously reduce steering delay requirements on a beamformer of the control system 104. Where the transducer array 102 takes the form of a flat array, the beamformer functionality of the control system 104 may be capable of producing sufficient delay to both steer and focus, for example operating the transducer elements of the transducer array 102 as a phased array. There are a large variety of other transducers and transducer array that may be employed. The claims should not be limited to any particular transducer or transducer array. Suitable transducer arrays 108 are commercially available from a variety of manufacturers and/or suppliers.

The control system 104 may provide several advanced features including synthetic aperture formation, frequency compounding, PW Doppler, color power, color flow (i.e., color velocity) and/or speckle reduction. The control system 104 may be capable of operating in A-, B-, M-, Doppler, energy, power, Doppler amplitude, color angio, or any other modes. The control system 104 may be capable of concurrently displaying information in more than one type of representation (e.g., triple or Echo/Doppler modes). The control system 104 may include a number of subsystems. For example, the control system 104 may include a transmit/receive subsystem 108, a transmit beamformer subsystem 110, a receive beamformer subsystem 112, a control subsystem 114, and a power subsystem 116.

The transmit/receive subsystem 108 may include one or more transmit/receive switches 108*a* (only one called out in FIG. 1) and optionally one or more matching networks (not illustrated). The transmit/receive subsystem 108 is communicatively coupled to the transducer elements of the transducer array 102. The transmit/receive switches 108*a* isolate the functions of transmission and reception. In particular, the transmit/receive switches 108*a* allow the elements of the transducer array 102 be selectively driven or to selectively receive representations of ultrasound return signals in the form of analog transducer element voltage signals or analog return signals. The transmit/receive subsystem 108 may be formed as a distinct ASIC. U.S. Pat. No. 5,893,363 titled ULTRASONIC ARRAY TRANSDUCER TRANSCEIVER FOR A HANDHELD ULTRASONIC DIAGNOSTIC INSTRUMENT describes such a transmit/receive ASIC. The transmit/receive ASIC may be positioned proximate the transducer array 102, for example within inches of the elements of the transducer array 102 to ensure short communications path.

The transmit beamformer subsystem 110 and receive beamformer subsystem 112 include transmit and timing control circuitry or implements transmit and timing control functionality, providing control signals to the transmit/receive subsystem 108 to control transmit waveform timing, aperture and focusing of the ultrasound pressure waves or beam. Each beamformer subsystem 110, 112 is discussed in more detail below.

The transmit beamformer subsystem 110 forms beams and drives the transducer elements of the transducer array 102 via the transmit/receive switches 108*a*. In particular, the transmit beamformer subsystem 110 may include one or more sets of modulators 118 and/or delay circuitry 120. The modulator(s) 118 may be controlled to generate digital drive signals, while the delay circuitry 120 may be controlled to delay the digital drive signals, for instance to allow steering and/or focusing of the ultrasound pressure waves transmitted from the transducer array 102. Notably, multiple pairs of modulators 118 and delay circuitry 120 may be employed. The transmit beamformer subsystem 110 may also include a one or more sets of digital-to-analog converters (DACs) 122 and amplifiers 124. The DACs 122 convert digital drive signals into an analog form, while the amplifiers 124 amplify the analog drive signals to provide high-voltage waveforms used to drive the transducer elements of the transducer array 102. Notably, multiple pairs of DACs 122 and amplifiers 124 may be employed. Additionally, the transmit beamformer subsystem 110 may also include one or more local processors, for instance local digital processor(s) 126. The local digital processor(s) 126 may take the form of digital signal processors (DSPs), application specific integrated circuits (ASICs), programmable (PGAs), microprocessors and/or other integrated devices as well as discrete devices or circuits. The local digital processor(s) 126 may be communicatively coupled to one or more of the other components of the transmit beamformer subsystem 110, as well as communicatively coupled to the central control subsystem 114. Multiple transmit beamformers or components thereof may advantageously allow the imaging system to successively acquire samples from multiple sample volumes.

The receive beamformer subsystem 112 beam forms the analog signals received from the individual transducer elements of the transducer array 102, received via the transmit/receive switches 108*a*, for example into a coherent scanline signal. In particular, receive beamformer subsystem 112 may include a one or more sets of amplifiers 128 and analog-to-digital converters (ADCs) 130. The amplifiers 128 amplify the analog signals (e.g., analog transducer element voltage signals), while the ADCs 130 convert the amplified analog signals into a digital form. For example, the amplifier(s) 128 may perform time gain compensation (i.e., TGC) to compensate for attenuation of ultrasound with depth. Notably, multiple pairs of amplifiers 128 and DACs 130 may be employed. The receive beamformer subsystem 112 may include one or more sets of apodization circuitry 132, interpolation circuitry 134, as well as delay circuitry 136. The apodization circuitry 132 may be used to accommodate for side lobes, for instance by decreasing relative sensitivity near the ends of a receiving surface of the transducer element(s). Additionally, or alternatively, relative excitation may be decreased if accommodated for via the transmit beamformer subsystem 110. The interpolation circuitry 134 may be used to perform interpolation, for instance to allow a change in sampling rate. The delay circuitry 136 may be controlled to delay various channels. Notably, multiple sets of apodization circuitry 132, interpolation circuitry 134, as well as delay circuitry 136 may be employed. The receive beamformer subsystem 112 may also include one or more local processors 138, for instance local digital processors. The local digital processor(s) 138 may take the form of DSPs, ASICs, PGAs, microprocessors and/or other integrated devices. The local digital processor(s) 138 may be communicatively coupled to one or more of the other components of the receive beamformer subsystem 112, as well as communicatively coupled to the central control subsystem 114. Additionally, the receive beamformer subsystem 112 may also include one or more summers or summer circuits 140 which sums the digitized return signals of the various channels.

While not specifically illustrated, the receive beamformer subsystem 112 may also include one or more filters or such may be implemented by one or more local digital processors 138. Thus, the receive beamformer subsystem 112 may filter the scanline signals, amplify the scanline signals, and/or processes the filtered scanline signals as B mode signals, Doppler signals, or both. Multiple receive beamformers and/or filters or components thereof may advantageously allow the imaging system to concurrently acquire samples from multiple sample volumes.

Normal sample volumes are typically one wavelength in duration. In some applications, a single sample volume may be much longer than sample volumes for conventional ultrasound imaging systems. In some applications sample volumes may partially overlap adjacent sample volumes. Thus, ultrasound imaging system described herein should have enough filtering and computational power to timely process multiple long sample volumes.

The control subsystem 114 may include a central controller 142, one or more memories or computer- or processor-readable storage mediums 144, and one or more buses 146 that couple the central controller 142 and the computer- or processor-readable storage mediums 144.

While illustrated as a single microprocessor, the central controller 142 may take the form of one or more microprocessors (e.g., Reduced Instruction Set or RISC processor), DSPs, PGAs or ASICs. The central controller 142 may execute instructions and/or program data stored on one or more computer- or processor-readable storage mediums 144, for example a program memory. The central controller 142 is communicatively coupled to the transmit beamformer subsystem 110 and receive beamformer subsystem 112 to control and synchronize the processing and control functions throughout the ultrasound imaging system 100. For example, the central controller 142 may coordinate process timing and loading of buffers and registers with the data necessary to perform the processing and display requested by the user. Timing for the central controller 142 may be provided by clock signals from the clock generator (not shown). It is to be recognized that the embodiments discussed herein are illustrative of only some of the possible embodiments. For example, the processing may be implemented in other ways and the processor(s) or other circuitry may be distributed in other manners or locations. For instance, a distributed architecture may be employed with communications occurring over one or more buses, networks or other communications mediums.

The computer- or processor-readable storage mediums 144 may take a variety of forms. For example, the computer- or processor-readable storage mediums 144 may include one or more Read Only Memories (ROM) 144a, Random Access Memories (RAM) 144b, or other volatile or non-volatile storage mediums such as FLASH memory, a magnetic disk (i.e., hard disk and drive), optical disk, etc. 144c. The computer- or processor-readable storage medium 144 may store data used by the transmit beamformer subsystem 110 or data produced by the receive beamformer subsystem 112.

The control subsystem 104 may further include a set of user controls 146. The display 106 and user controls 146 may form all or part of a user interface. The user controls 146 may allow a user to turn the ultrasound imaging system 1000N and OFF, enter time, date, and/or patient data, interact with a graphical user interface that includes user selectable icons or elements of a menu (e.g., pull down menu, popup menu), and/or select or set various operating characteristics such as an operating mode (e.g., B mode, Doppler), color Doppler sector or frame rate, and special functions.

The central controller 142 is operated under user control by commands, selections and/or entries made by the user via the user controls 146. As described above, the user controls 146 allow a user to direct and control the operations of the ultrasound imaging system 100. Where a handheld form factor is employed, a number of functions, such as patient data entry, Cineloop® operation, and 3D review, may be operated through menu control provided via a graphical user interface. Such may advantageously minimize the number of keys, buttons or switches present on a small handheld housing.

Additionally, or alternatively, a number of operational functions may be programmed to be logically associated with specific diagnostic applications. Such operational functions may be automatically executed or performed when a specific operating mode or application is selected by a user. For example, selection of B mode imaging may automatically invoke frequency compounding and depth dependent filtering, while selection of Doppler operation may cause automatic set up of a four multiplier filter as a wall filter. The menu selection of specific clinical applications can, for example, automatically invoke specific feature settings such as TGC control characteristics and focal zones.

The central controller 142 and possibly other controllers or circuitry receives the ultrasound B mode and Doppler information from the receive beamformer subsystem 112. The central controller 142 and possibly other controllers or circuitry may perform a scan conversion that produces video output signals or frames of video. The central controller 142 and possibly other controllers or circuitry may be configured to add alphanumeric information to the video or other image data, such as the time and/or date via a time and/or date function, and patient identification. An optional graphics processor (not shown) may overlay the ultrasound images with information such as depth and focus markers and cursors. Frames of ultrasound images may be stored in a dedicated video memory (not shown). Such may allow selected frames to be recalled and replayed, for instance in a live Cineloop® real-time sequence. Video information may be available at a video output. The video information may be made available in a variety of formats, for instance NTSC and PAL formats or RGB drive signals for the display 106 or other a video monitor.

The control subsystem 104 may include one or more communications interfaces 148 to which the central controller 142 may be communicatively coupled. The communications interfaces 148 may take a variety of forms for instance a communications port (e.g., Universal Serial Bus or USB port, Ethernet port, FIREWIRE® port, infrared transmitter/receiver). The communications interface 148 allows other modules and functions to be communicatively coupled to or communicate with the ultrasound imaging system 100. The communications interface 148 can communicatively couple to a modem or communications link to transmit and receive ultrasound images, ultrasound information and/or other information from remote locations. The communications interface 148 can accept other data storage devices to add new functionality to the ultrasound device, for instance an ultrasound information analysis package. The communications interface 148 may also allow the central controller 142 to access additional program instructions or data and/or transmit image information remotely.

The ultrasound imaging system 100 may include a power subsystem 116 that applies power (e.g., battery power) to the other components and subsystems of the ultrasound imaging system 100. For example, the power subsystem 116 may monitor and control electrical power applied to the transducer array 102, thereby controlling the acoustic energy which is applied to the patient. The power subsystem 116 may also be configured to minimize overall power consumption of the ultrasound imaging system 100. The power subsystem 116 may provide electrical power from a portable power storage device (e.g., rechargeable battery cells, ultra-capacitor array, fuel cell array), particularly where the ultrasound imaging system 100 takes the form of a handheld or portable device. The power subsystem 116 may include a DC-DC converter to convert the low battery voltage to a higher voltage which is applied to the transmit/receive subsystem 108 to drive the elements of the transducer array 102. The power subsystem 116 may include a rectifier and step down converter to convert AC power to recharge the power storage device (e.g., rechargeable battery cells, ultra-capacitor array).

The display 106 may take a variety of forms, for example a liquid crystal display (LCD). The display 106 may be integrated into a common housing with the control system 104 and/or the transducer array 102, or may be separate.

While the various components are generally described above as being housed in a single unitary or single piece housing, other alternatives will be readily apparent from this description. For instance, some of the subsystems could be located in a common enclosure, with the beamformer subsystems 110, 112 physically and/or communicatively detachably coupled to the transducer elements of the transducer array 102. This allows different transducer arrays to be used with a digital beamformer, digital filter, and image processor for various diagnostic imaging procedures. Alternatively, the transducer array 102, transmit/receive subsystem 108 and transmit and receive beamformer subsystems 110, 112 could be housed in a transducer housing, with the control subsystem 104 including user controls 146 housed in a separate housing along with the display 106. Various suitable structures and methods are described in U.S. Pat. No. 7,604,596 and U.S. Pat. No. 5,817,024. Other configurations of the ultrasound imaging system 100 may be employed.

As previously discussed, ultrasound information may be used to adjust operation of the ultrasound imaging system. For example, a focus or direction of further ultrasound sample volumes may be adjusted. For instance, from time-to-time various sample volumes may be evaluated with respect to a desired location (e.g., particular anatomical structure, reference, region of interest). Such may include a sample volume that was previously centered or best coincided with the desired location, such sample volume referred to as the principal sample volume. Such may also include other sample volumes axially and/or laterally disposed with respect to the principal sample volume, referred to as additional sample volumes. In response to the evaluation, a different sample volume may be identified or selected as a new principal sample volume or the same sample volume may be reused as the principal sample volume. Likewise, the additional sample volumes may be updated or reused accordingly. This may be done by acquiring sample volumes in the lateral and/or axial directions, without incurring significant increases in acquisition time, thus avoiding significant decreases in pulse repetition frequency (PRF) rates.

In particular, acquiring additional sample volumes at shallower depths in the same axial direction as the principal sample volume can be achieved with incurring any additional "pings" or acquisition time, thereby having no effect on PRF rate, since the same sample data can be used and filtered for several different sample volume depths. Acquiring additional sample volumes at deeper depths in the same axial direction as the principal sample volume will add a small amount of additional acquisition time, but should not be so significant as to hinder operation or substantially decrease temporal resolution.

The ultrasound imaging system 100 may employ conventional multiline acquisition techniques to acquire additional sample volumes in the lateral directions from the principal sample volume or principal axial ray. To accomplish such, the ultrasound imaging system 100 may advantageously include multiple receive beamformers 112 to acquire samples volumes to either side (e.g., left and right in FIGS. 2-4) of a principal axial ray. Multiple sample volumes may be acquired at different axial depths along the additional axial rays laterally disposed from the principal axial ray, in a fashion similar to that for the principal axial ray.

Figure 2:
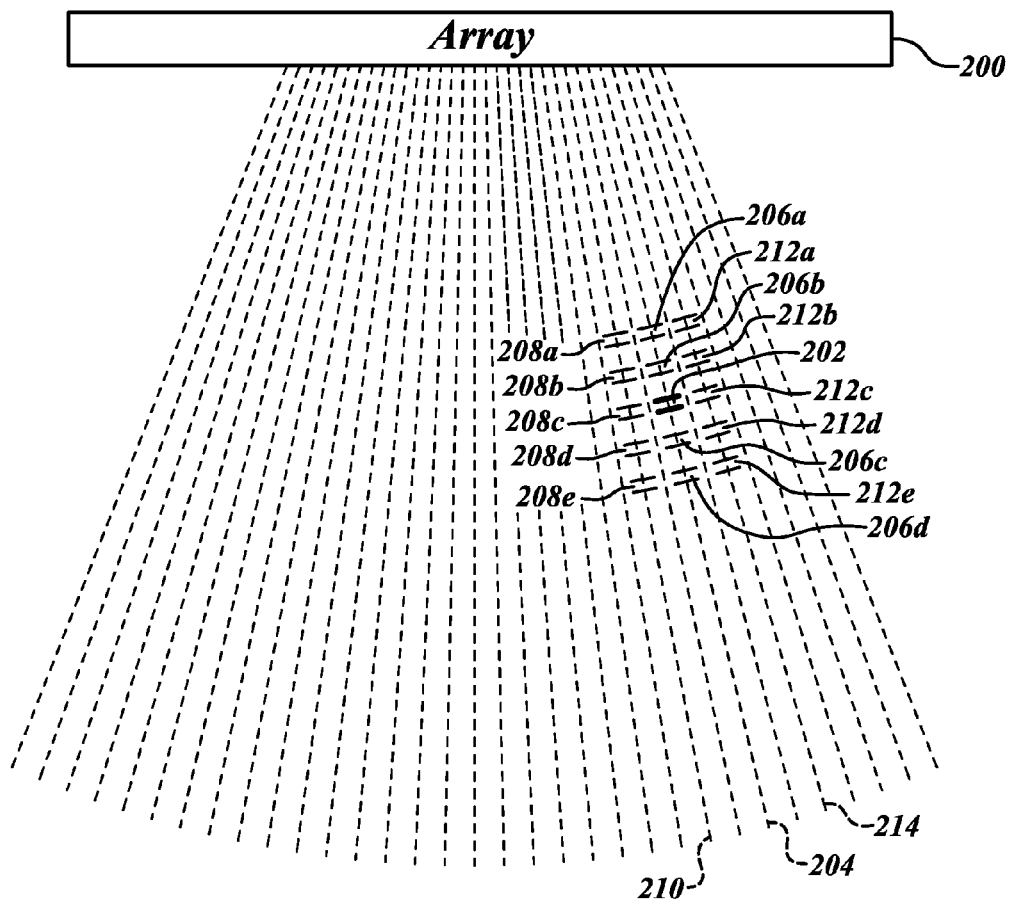
FIG. 2 is a schematic diagram of a transducer array transmitting ultrasound pressure waves into a medium during a first period according to one illustrated embodiment, illustrating an initial principal sample volume, a number of additional sample volumes axially disposed with respect to the initial principal sample volume and a number of additional sample volumes laterally disposed with respect to the initial principal sample volume.
Figure 3:
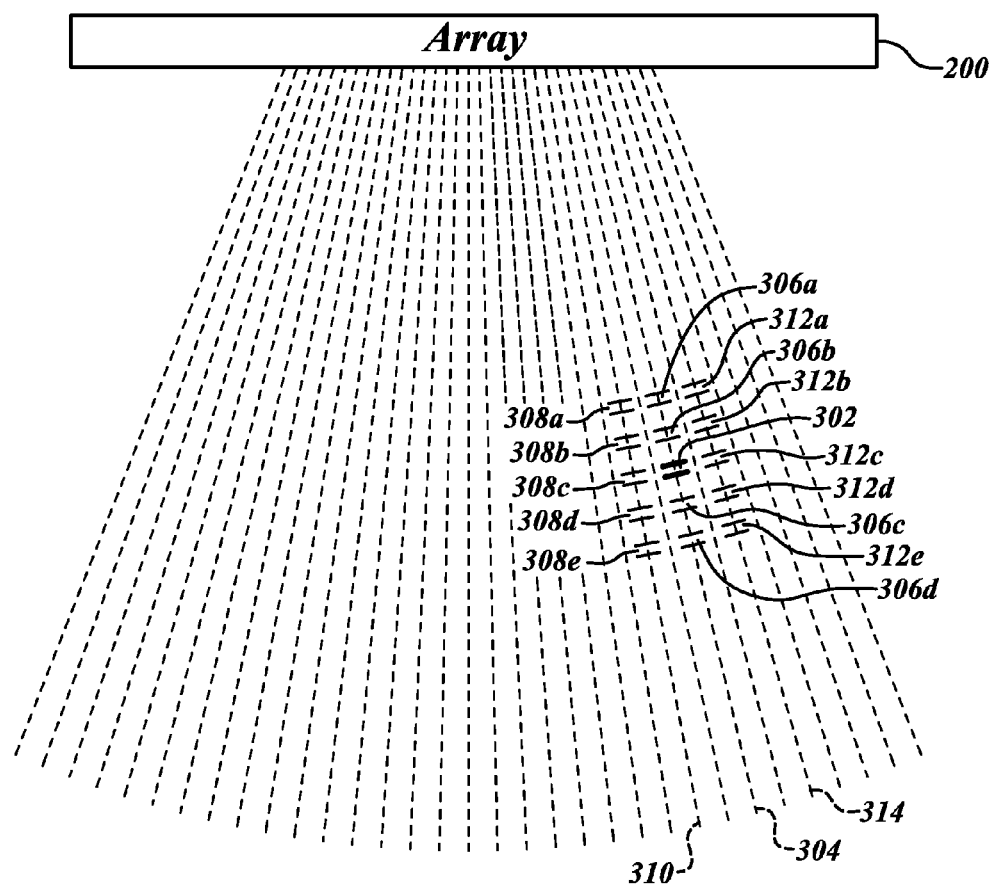
FIG. 3 is a schematic diagram of a transducer array transmitting ultrasound pressure waves into a medium during a second period according to one illustrated embodiment, illustrating an new principal sample volume axially displaced from the initial principal sample volume, a number of additional sample volumes axially disposed with respect to the new principal sample volume and a number of additional sample volumes laterally disposed with respect to the new principal sample volume.
Figure 4:
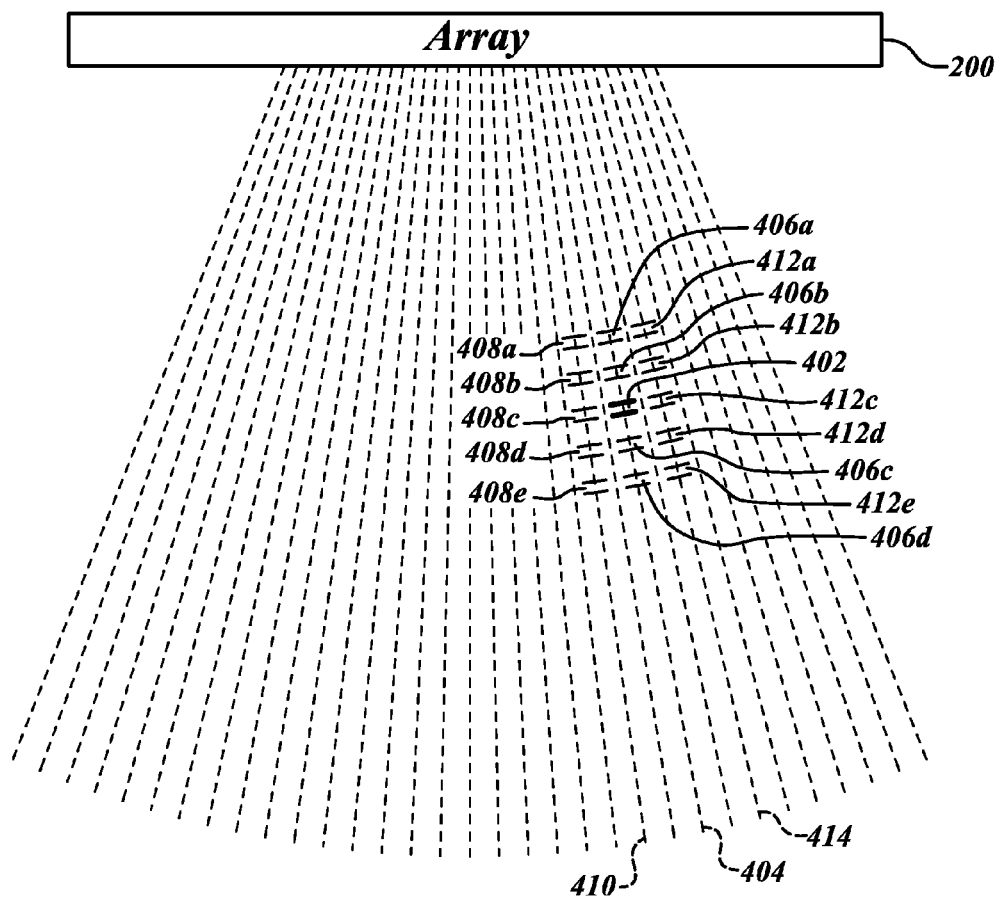
FIG. 4 is a schematic diagram of a transducer array transmitting ultrasound pressure waves into a medium during a third period according to one illustrated embodiment, illustrating an new principal sample volume laterally displaced from the initial principal sample volume, a number of additional sample volumes axially disposed with respect to the new principal sample volume and a number of additional sample volumes laterally disposed with respect to the new principal sample volume.

FIGS. 2-4 illustrate various approaches to acquiring additional sample volumes around a principal or main sample volume.

FIG. 2 shows a transducer array 200 transmitting ultrasound illustrated as axial rays extending into a medium during a first period, according to one illustrated embodiment. While illustrated in two-dimensions, those of ordinary skill in the art will appreciate that ultrasound image sampling may take place in three-dimensions.

In particular, FIG. 2 shows an initial principal sample volume 202 that is being sampled, at a first axial depth along an initial principal axial ray 204. As illustrated in FIG. 2, a number of initial additional sample volumes may be sampled at different axial depths along the same initial principal axial ray 204. These are illustrated as four initial additional sample volumes 206a-206d (collectively 206), with pairs 206a, 206d, 206b, 206c of these initial additional sample volumes axially diametrically opposed to one another on either side of the initial principal sample volume 202.

Also as illustrated in FIG. 2 a number of initial additional sample volumes may be sampled, laterally disposed from the initial principal sample volume 202. These are illustrated as five initial sample volumes 208a-208e (collectively 208) on a first lateral axial ray 210 laterally disposed on one side of the initial principal axial ray 204, and five initial sample volumes 212a-212e (collectively 212) on a second lateral axial ray 214 laterally disposed on the other side of the initial principal axial ray 204. Pairs of the additional sample volumes 208, 212 may be diametrically opposed from one another across respective ones of the initial sample volumes 202, 206 on the principal axial ray 204. As will be apparent from the teachings here to those of ordinary skill in the art, greater or fewer sample volumes may be used. Additionally, or alternatively, the number of sample volumes on one axial ray may differ from the number of sample volumes on another axial ray. As previously noted, ultrasound image sampling may take place in three-dimensions. Hence additional sample volumes 206 may be arrayed about the principal axis 204 at various angular locations. Thus, for example a set of additionally sample volumes may be sampled in a plane that is orthogonal to the plane of the drawing sheet. Again, such additional samples in the orthogonal plane may be diametrically opposed with respect to one another across the principal axial ray 204 or sample volume 202.

FIG. 3 shows a transducer array 200 transmitting ultrasound illustrated as axial rays extending into a medium during a second period, according to one illustrated embodiment.

In particular, FIG. 3 shows a new principal sample volume 302 that is being sampled at a second axial depth along a principal axial ray 304. Notably, the second axial depth is different from the first axial depth (FIG. 2). As illustrated in FIG. 3, a number of new additional sample volumes may be sampled at different axial depths along the same initial principal axial ray 304. These are illustrated as four new additional sample volumes 306a-306d (collectively 306), with pairs of these new additional sample volumes axially diametrically opposed to one another on either side of the new principal sample volume 302.

Also as illustrated in FIG. 3 a number of new additional sample volumes may be sampled, laterally disposed from the new principal sample volume 302. These are illustrated as five new sample volumes 308a-308e (collectively 308) on a first lateral axial ray 310 laterally disposed on one side of the principal axial ray 304, and five new sample volumes 312a-312e (collectively 312) on a second lateral axial ray 314 laterally disposed on the other side of the principal axial ray 304, diametrically opposed from one another across respective ones of the new sample volumes 302, 306 on the principal axial ray 304. Thus, a new principal sample volume 302 is sampled along with new additional sample volumes 306, 308, 312 axially and/or laterally disposed with respect to the new principal sample volume 302. As previously noted, greater or fewer sample volumes may be used and the number of sample volumes on one axial ray may differ from the number of sample volumes on another axial ray. The comments regarding operation in a three-dimensional space made with respect to FIG. 2 apply to this illustrated embodiment as well.

FIG. 4 shows a transducer array 200 transmitting ultrasound illustrated as axial rays extending into a medium during a third period, according to one illustrated embodiment.

In particular, FIG. 4 shows a new principal sample volume 402 that is being sampled at a new principal axial ray 404. Notably, the new principal axial ray 404 is different from the initial principal axial ray 204 (FIG. 2). As illustrated in FIG. 4, a number of new additional sample volumes may be sampled at different axial depths along the same new principal axial ray 404. These are illustrated as four new additional sample volumes 406a-406d (collectively 406), with pairs of these new additional sample volumes axially diametrically opposed to one another on either side of the new principal sample volume 402.

Also as illustrated in FIG. 4 a number of new additional sample volumes may be sampled, laterally disposed from the new principal sample volume 404. These are illustrated as five new sample volumes 408a-408e (collectively 408) on a first lateral axial ray 410 laterally disposed on one side of the new principal axial ray 404, and five new sample volumes 412a-412e (collectively 412) on a second lateral axial ray 414 laterally disposed on the other side of the new principal axial ray 404, diametrically opposed from one another across respective ones of the new sample volumes 402, 406 on the new principal axial ray 404. Thus, a new principal sample volume 402 is sampled along with new additional sample volumes 406, 408, 412 axially and/or laterally disposed with respect to the new principal sample volume. As previously noted, greater or fewer sample volumes may be used and the number of sample volumes on one axial ray may differ from the number of sample volumes on another axial ray. The comments regarding operation in a three-dimensional space made with respect to FIG. 2 apply to this illustrated embodiment as well.

Figure 5:
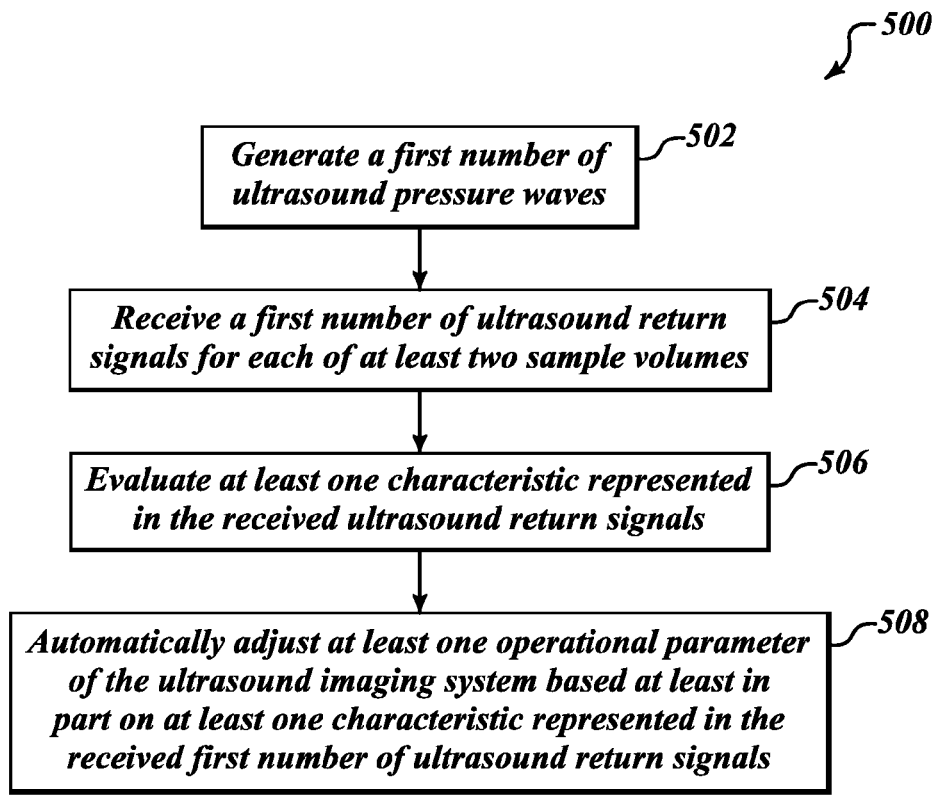
FIG. 5 is a high level flow diagram of a method of operating an ultrasound imaging system according to one illustrated embodiment which includes sampling at least two different sample volumes and adjusting at least one operation parameter of the ultrasound imaging system based at least in part on characteristics represented in received ultrasound return signals.

FIG. 5 shows a method 500 of operating an ultrasound imaging system, according to one illustrated embodiment.

At 502, the ultrasound imaging system generates a first number of ultrasound pressure waves. For example, a transmit beamformer subsystem may generate drive signals, causing one or more of the transducer elements of a transducer array to transmit ultrasound pressure waves. As previously noted, these may be focused and/or directed. In particular, the ultrasound pressure waves may be generated to sample certain sample volumes along one or more axial rays, at one or more axial depths.

At 504, the ultrasound imaging system receives a first number of ultrasound return signals for each of at least two sample volumes in response to the first number of ultrasound pressure waves. The two sample volumes have at least respective portions thereof that are at least one of axially displaced and/or laterally displaced with respect to one another. For example, a receive beamformer subsystem may receive and process analog signals produced by the transducer array in response to ultrasound return signals.

At 506, the ultrasound imaging system evaluates at least one characteristic represented in the received ultrasound return signals. For example, the ultrasound imaging system may evaluate one or more values that are indicative of a power, a variance, a velocity, and/or a set of echo data. Such information may represent structures of interest, for example a vein or artery, bone, organ, flow of blood or other fluid, or may represent some other structure of interest. For instance, it may be desirable to maintain the principal sample volume at least partially coincident with some defined region of interest (ROI). This may be particularly desirable where there is some relative movement between the transducer array and the object being sampled. For instance, it may be desirable to maintain the principal sample volume coincident with some bodily structure where the transducer array is being moved, or the bodily structure moves or is being moved. Also for instance, it may be desirable to maintain the principal sample volume along a centerline of an artery, even where the artery is tortuous and/or the transducer array is being scanned along a body.

The characteristics, also referred to as parameters, may all be computed from the same acquired data or ultrasound information. As an example, velocity may be fastest in the center of a vessel. Thus, velocity information may be evaluated to determine the location of a centerline of a vessel, and the principal sample volume moved or selected to be coincident, or at least partially coincident with the centerline as determined based on velocity. For instance, the measured or determined velocity may be compared to some threshold or to velocity measured or determined at other locations. In some instance, power may be a better indicator of certain structure, such as the centerline of vessel carrying blood or other fluid. Hence, the measured or determined power may be compared to some threshold or to power measured or determined at other locations. In other instances, variance or some other measure of turbulence may be suitable for indicating a location or presence of a particular structure (e.g., blockage or plaque buildup). Hence, variance may be evaluated against some threshold and/or against turbulence at other locations. Thus, the ultrasound imaging system should be capable of processing multiple sample volumes, as well as background echo data, from the same acquired ultrasound return signals. In addition, or alternatively, to evaluating characteristics such as power, a variance, a velocity, echo data may be computed for each axial ray. Using echo information and/or "Doppler" (e.g., pulse wave "Doppler") information may allow locations of certain structures to be determined or computed. For example, the location of vessel walls may be determined or computed to aid in selecting which of the currently acquired sample volumes will be the new principal sample volume (e.g., new center sample volume). Thus, for example, the new principal sample volume may be placed coincident or at least partially coincident with a centerline of some structure indicated by echoes alone, by one or more "Doppler" parameters, and/or a combination of echoes and "Doppler" parameters such as velocity, power and/or variance. Thus, the ultrasound imaging system should be capable of processing multiple sample volumes, as well as background echo data, from the same acquired ultrasound return signals. The ultrasound imaging system may employ some of its transmissions (e.g., "pings") to acquire two-dimensional ultrasound data and some of its transmission to acquire Doppler ultrasound data. Thus, one ray may be used to capture background image information (e.g., pulse echo) while another ray used to capture pulse wave Doppler information.

At 508, the ultrasound imaging system adjusts at least one operational parameter based at least in part on at least one characteristic represented in the received first number of ultrasound return signals. The adjustment may be automatic or not. For example, the ultrasound imaging system may adjust the transmit beamformer to move or change a location of a principal sample volume. For instance, the ultrasound imaging system may cause a new principal sample volume to be axially displaced with respect to an initial or previous principal sample volume. Alternatively or additionally, the ultrasound imaging system may cause a new principal sample volume to be laterally displaced with respect to an initial or previous principal sample volume. Also for example, the ultrasound imaging system may adjust the transmit beamformer to move or change a location of an additional (i.e., supplemental or not principal) sample volume. For instance, the ultrasound imaging system may cause a new additional sample volume to be axially displaced with respect to an initial or previous additional sample volume. Alternatively or additionally, the ultrasound imaging system may cause a new additional sample volume to be laterally displaced with respect to an initial or previous additional sample volume. Such may, for instance, move the principal sample volume to be centered with respect to some structure, such as an artery. Thus, where one of the additional sample volumes is identified or selected as the new principal sample volume, then the ultrasound transmissions from the transducer array may be redirected and/or refocused to be centered on the new principal sample volume.

Figure 6:
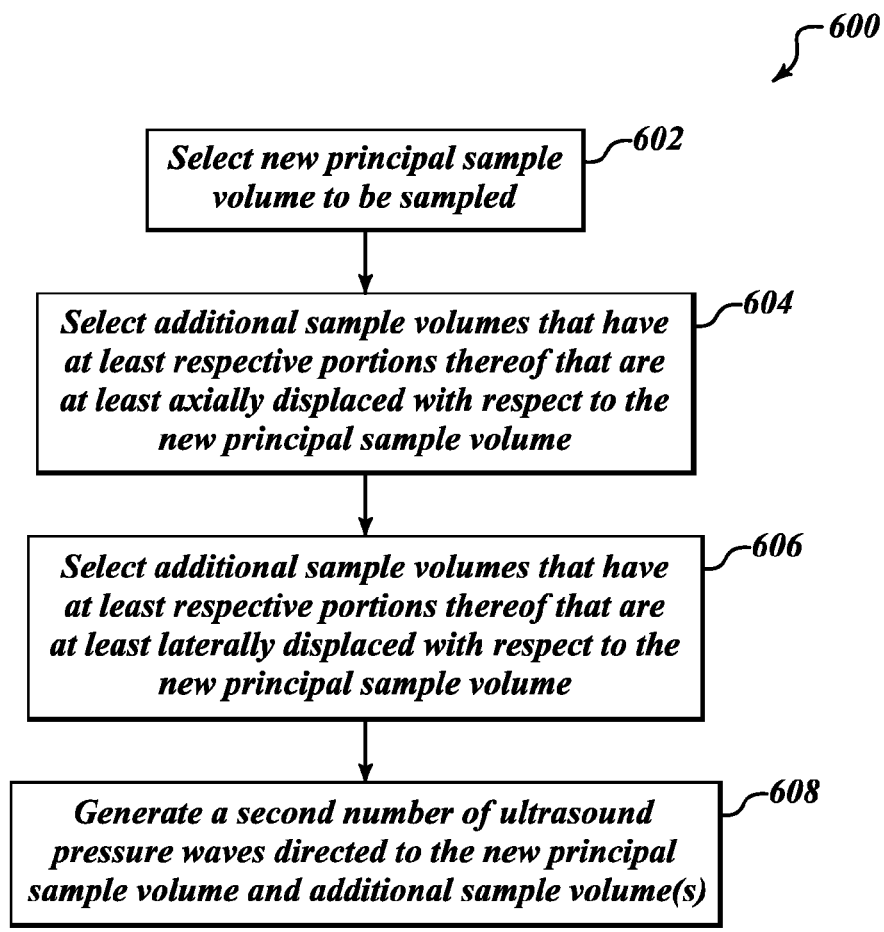
FIG. 6 is a low level flow diagram of a method of adjusting at least one operation parameter of the ultrasound imaging system based at least in part on characteristics represented in received ultrasound return signals according to one illustrated embodiment, in accordance with the method of FIG. 5.

FIG. 6 shows a method 600 of operating an ultrasound imaging system, according to one illustrated embodiment. The method 600 may, for example, be executed as part of the method 500 (FIG. 5).

At 602, the ultrasound imaging system selects a new principal sample volume to be sampled. For example, the ultrasound imaging system may select one of the at least two initial sample volumes as the new principal sample volume. Thus, for instance, one of the additional sample volumes may meet a desired criteria (e.g., coincident or centered with respect to some region or interest, structure or reference), and hence will be used as the new principal sample volume. In some instances, the previous principal sample volume may still meet the desired criteria, and the same principal sample volume will be sampled.

Optionally, at 604, the ultrasound imaging system selects one or more additional sample volumes to be sampled. These additional sample volumes have at least respective portions thereof that are at least axially displaced with respect to the new principal sample volume. For example, the ultrasound imaging system may select at least two additional sample volumes to be sampled that have at least respective portions thereof that are axially opposed to one another across the new principal sample volume. In some instances, the entire additional sample volumes will be axially displaced from the entire principal sample volume.

Optionally, at 606, the ultrasound imaging system selects additional sample volumes to be sampled that have at least respective portions thereof that are at least laterally displaced with respect to the new principal sample volume. For example, the ultrasound imaging system may select at least two additional sample volumes to be sampled that have at least respective portions thereof that are laterally opposed to one another across the new principal sample volume. In some instances, the entire additional sample volumes will be laterally displaced from the entire principal sample volume.

At 608, the ultrasound imaging system generates a second number of ultrasound pressure waves directed to the new principal sample volume and at least one of the additional sample volume(s). The method 600 may then repeat, substituting new principal and/or additional sample volumes for initial or previous principal and/or additional sample volumes.

Figure 7:
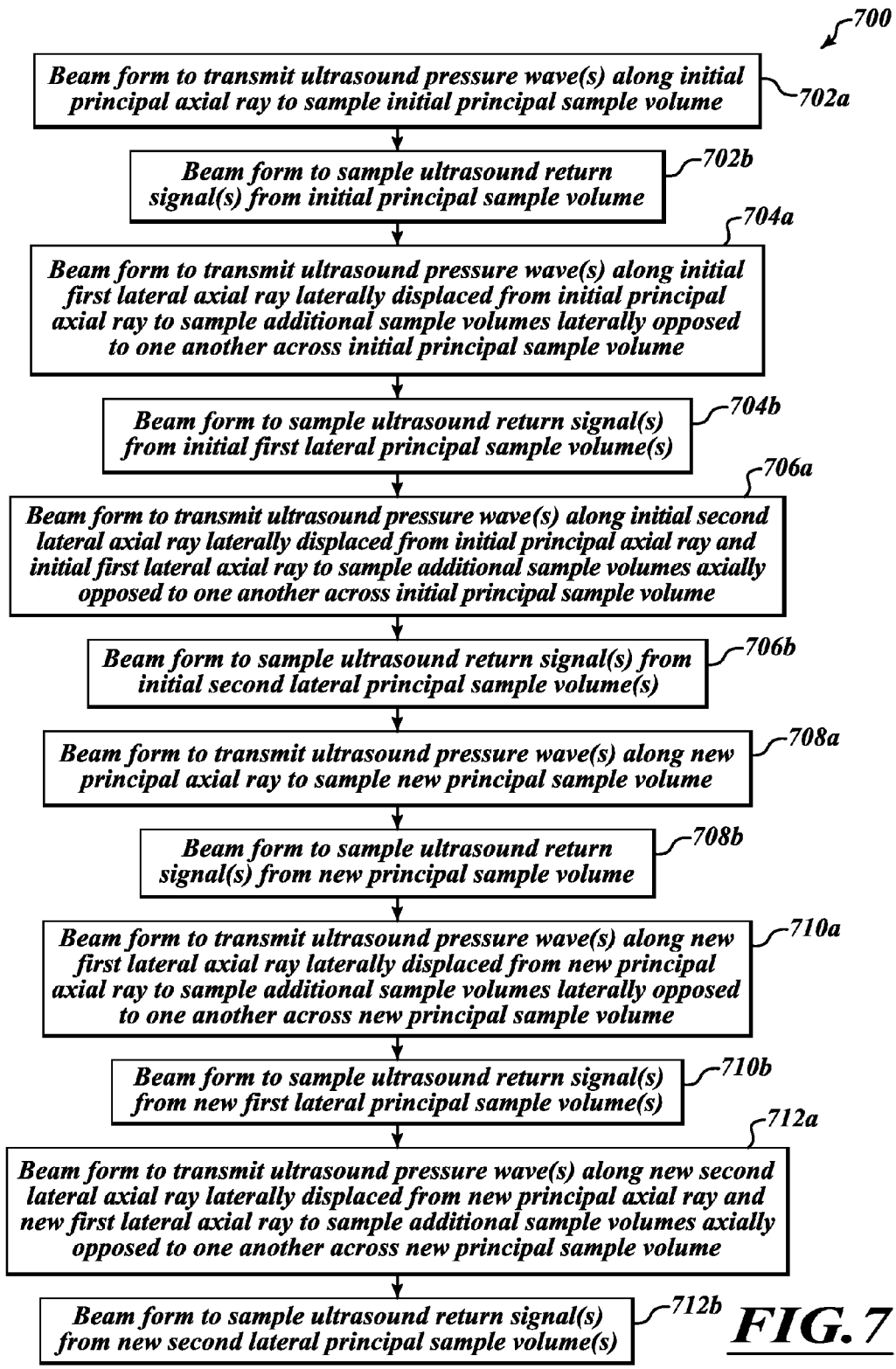
FIG. 7 is a low level flow diagram of a method of operating an ultrasound imaging system according to one illustrated embodiment including beam forming to sample an initial principal sample volume and initial additional sample volumes, and beam forming to sample new principal sample volume and new additional sample volumes, in accordance with the method of FIG. 5.

FIG. 7 shows a method 700 of operating an ultrasound imaging system, according to one illustrated embodiment. The method 700 may, for example, be executed as part of the method 500 (FIG. 5).

At 702a, the ultrasound imaging system transmit beam forms to transmit at least one ultrasound pressure wave along an initial principal axial ray to sample an initial principal sample volume. For example, a transmit beamformer subsystem may produce drive signals to cause a transducer array to transmit ultrasound pressure waves along the principal axial array focused at a desired depth.

At 702b, the ultrasound imaging system receive beam forms to receive at least one ultrasound return or echo signal in response to the ultrasound pressure wave transmitted along the initial principal axial ray to sample the initial principal sample volume. For example, a receive beamformer subsystem may filter and otherwise process the ultrasound return signals to produce image data and to determine information (e.g., echo and/or "Doppler" characteristics or parameters) represented in the ultrasound return signals, focused at one or more desired depths.

At 704a, the ultrasound imaging system transmit beam forms to transmit at least one ultrasound pressure wave along an initial first lateral axial ray laterally displaced from the initial principal axial ray. For example, a transmit beamformer subsystem may produce drive signals to cause a transducer array to transmit ultrasound pressure waves along an axial ray laterally disposed with respect to the principal axial ray and focused one or more desired depths.

At 704b, the ultrasound imaging system receive beam forms to receive at least one ultrasound return or echo signal in response to the ultrasound pressure wave transmitted along the initial first lateral axial ray. For example, a receive beamformer subsystem may filter and otherwise process the ultrasound return signals to produce image data and to determine information (e.g., echo and/or "Doppler" characteristics or parameters) represented in the ultrasound return signals, focused at one or more desired depths.

At 706a, the ultrasound imaging system transmit beam forms to transmit at least one ultrasound pressure wave along an initial second lateral axial ray laterally displaced from the initial principal axial ray and the initial first lateral axial ray. For example, a transmit beamformer subsystem may produce drive signals to cause a transducer array to transmit ultrasound pressure waves along an axial ray laterally disposed with respect to the principal axial ray and focused one or more desired depths.

At 706b, the ultrasound imaging system receive beam forms to receive at least one ultrasound return or echo signal in response to the ultrasound pressure wave transmitted along the initial second lateral axial ray. For example, a receive beamformer subsystem may filter and otherwise process the ultrasound return signals to produce image data and to determine information (e.g., echo and/or "Doppler" characteristics or parameters) represented in the ultrasound return signals, focused at one or more desired depths.

Thus, the ultrasound imaging system may, for example, sample at least two additional sample volumes, laterally opposed to one another across the initial principal sample volume.

At 708a, the ultrasound imaging system transmit beam forms to transmit at least one ultrasound pressure wave along a new principal axial ray to sample a new principal sample volume. The new principal axial ray may be different from the initial principal axial array.

At 708b, the ultrasound imaging system receive beam forms to receive at least one ultrasound return or echo signal in response to the ultrasound pressure wave transmitted along the new principal axial ray to sample the new principal sample volume. For example, a receive beamformer subsystem may filter and otherwise process the ultrasound return signals to produce image data and to determine information (e.g., echo and/or "Doppler" characteristics or parameters) represented in the ultrasound return signals, focused at one or more desired depths.

At 710a, the ultrasound imaging system transmit beam forms to transmit at least one ultrasound pressure wave along a new first lateral axial ray laterally displaced from the new principal axial ray. For example, a transmit beamformer subsystem may produce drive signals to cause a transducer array to transmit ultrasound pressure waves along a new first lateral axial ray laterally disposed with respect to the new principal axial ray and focused one or more desired depths.

At 710b, the ultrasound imaging system receive beam forms to receive at least one ultrasound return or echo signal in response to the ultrasound pressure wave transmitted along the new first lateral axial ray. For example, a receive beamformer subsystem may filter and otherwise process the ultrasound return signals to produce image data and to determine information (e.g., echo and/or "Doppler" characteristics or parameters) represented in the ultrasound return signals, focused at one or more desired depths.

At 712a, the ultrasound imaging system transmit beam forms to transmit at least one ultrasound pressure wave along a new second lateral axial ray laterally displaced from the new principal axial ray and the new first lateral axial ray to sample at least two additional sample volumes axially opposed to one another across the new principal sample volume.

At 712b, the ultrasound imaging system receive beam forms to receive at least one ultrasound return or echo signal in response to the ultrasound pressure wave transmitted along the new second lateral axial ray. For example, a receive beamformer subsystem may filter and otherwise process the ultrasound return signals to produce image data and to determine information (e.g., echo and/or "Doppler" characteristics or parameters) represented in the ultrasound return signals, focused at one or more desired depths.

Thus, the ultrasound imaging system may, for example, sample at least two additional sample volumes, laterally opposed to one another across the new principal sample volume. Hence, the ultrasound imaging system may, for example, beam form to transmit the ultrasound pressure waves along at least three axial rays, the three axial rays laterally spaced from one another.

FIG. 8 shows a two-dimensional ultrasound image 800 which may be produced by an ultrasound imaging system according to one illustrated embodiment.

The two-dimensional ultrasound image 800 (e.g., B-mode image) represents a structure 802, for example a bodily tissue such as an artery. As illustrated, a region of interest (ROI) 804 may be defined in the two-dimensional ultrasound image 800. The ROI 804 may be defined in a number of manners. For example, an operator may define a desired ROI 804 using a cursor and user controls. Also for example, an ROI 804 may be defined based on certain criteria or characteristics represented in the information (e.g., echo and/or "Doppler") captured by the ultrasound imaging system.

FIG. 9 shows a method 900 of operating an ultrasound imaging system, according to one illustrated embodiment.

The method 900 may, for example, be executed as part of the method 500 (FIG. 5). The method 900 may adjust a location of a principal sample volume or select a new principal sample volume selected so as to remain focused on an identified ROI.

At 902, the ultrasound imaging system selects new principal sample volume to at least partially coincide with an ROI 804 (FIG. 8) in an object being imaged.

At 904, the ultrasound imaging system selects additional sample volume(s) to be sampled that have at least respective portions thereof that are at least one of axially displaced and/or laterally displaced with respect to the new principal sample volume.

FIG. 10 shows a two-dimensional ultrasound B-mode image 1000 and a two-dimensional spectral "Doppler" trace 1002 which may be produced by an ultrasound imaging system according to one illustrated embodiment. Such may be displayed by an ultrasound imaging system operating in an echo/Doppler mode.

The two-dimensional B-mode ultrasound image 1000 represents a structure 1004, for example a bodily tissue such as an artery. As illustrated, a current principal sample volume 1006 may be defined in the two-dimensional ultrasound image 1000. The current principal sample volume 804 represents a volume currently being sampled at a particular range of depths.

The spectral Doppler trace 104 represents a distribution of frequencies in a "Doppler" signal, which may be employed in determining velocity of a tissue, for example velocity of a bodily fluid such as blood in an artery or velocity of a valve such as a mitral valve in the heart.

FIG. 11 shows a method 1100 of operating an ultrasound imaging system, according to one illustrated embodiment. The method 1100 may, for example, be executed as part of the method 500 (FIG. 5). The method 110 may adjust a location of principal sample volume or select a new principal sample volume so as to maintain the principal sample volume relative to some structure. Such may, for example, allow the principal sample volume to be maintained in the center of an artery 1004 (FIG. 10), as the transducer array is moved along the artery while looking for changes in blood flow.

At 1102, the ultrasound imaging system selects new principal sample volume 1006 (FIG. 10) to be centered with respect to at least one structure 1104 (FIG. 10) of an object being imaged.

At 1104, the ultrasound imaging system selects additional sample volume(s) to be sampled that have at least respective portions thereof that are at least one of axially displaced and/or laterally displaced with respect to the new principal sample volume.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other ultrasound systems, not necessarily the exemplary ultrasound imaging system generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via ASICs. However, those skilled in the art will recognize that the embodiments disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors), as one of more PGAs such as field programmable gate arrays (FPGAs), as other firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any physical computer-readable medium for use by or in connection with any processor-related system or method. In the context of this disclosure, a memory is a computer-readable medium that is an electronic, magnetic, optical, or other physical device or means that contains or stores a computer and/or processor program. Logic and/or the information can be embodied in any computer-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "computer-readable medium" can be any physical element that can store the program associated with logic and/or information for use by or in connection with the instruction execution system, apparatus, and/or device. The computer-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a RAM, ROM, an erasable programmable read-only memory (EPROM, EEPROM, or Flash memory), a portable compact disc read-only memory (CDROM), digital tape.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Pat. No. 5,893,363 and U.S. Pat. No. 7,604,596 are incorporated herein by reference, in their entirety. Aspects of the embodiments can be modified, if necessary, to employ systems, circuits and concepts of the various patents, applications and publications to provide yet further embodiments.

One of ordinary skill in the art will recognize that any one or more of the acts or structures recited in any of the dependent claims could be included in the independent claim, the remaining dependent claims depending off the modified independent claim. That is, while the dependent claims set out specific acts and structures, such acts and structures may be combined in any combination or permutation.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of operating an ultrasound imaging system, comprising:
    generating a number of ultrasound pressure waves;
    receiving a number of ultrasound return signals from a principal sample volume and at least one additional sample volume that is axially or laterally displaced with respect to the principal sample volume;
    determining a characteristic of the return signals in the principal sample volume and the at least one additional sample volume; and
    selecting a new principal sample volume by moving or changing a location of the principal sample volume with a control circuit based at least in part on the determined characteristic of the return signals from the principal sample volume or the at least one additional sample volume.

2. The method of claim 1, further comprising:
    generating a second number of ultrasound pressure waves directed to the new principal sample volume and at least one additional sample volume that is axially displaced or laterally displaced with respect to the new principal sample volume.

3. The method of claim 1 further comprising:
    selecting at least two additional sample volumes to be sampled that have at least respective portions thereof that are laterally opposed to one another across the new principal sample volume.

4. The method of claim 1 wherein selecting a new principal sample volume includes selecting an additional sample volume as the new principal sample volume.

5. The method of claim 1 wherein selecting a new principle sample volume includes:
    selecting an additional sample volume as a new principal sample volume.

6. The method of claim 1, further comprising:
    beam forming to sample the new principal sample volume;
    beam forming to sample at least two additional sample volumes that have at least respective portions thereof that are axially opposed to one another across the new principal sample volume; and
    beam forming to sample at least two additional sample volumes that have at least respective portions thereof that are laterally opposed to one another across the new principal sample volume.

7. The method of claim 1 wherein generating a first number of ultrasound pressure waves includes:
    transmit beam forming to transmit at least one ultrasound pressure wave along an initial principal axial ray;
    transmit beam forming to transmit at least one ultrasound pressure wave along an initial first lateral axial ray laterally displaced from the initial principal axial ray; and
    transmit beam forming to transmit at least one ultrasound pressure wave along an initial second lateral axial ray laterally displaced from the initial principal axial ray and the initial first lateral axial ray.

8. The method of claim 7, further comprising:
    transmit beam forming to transmit at least one ultrasound pressure wave along a new principal axial ray;

transmit beam forming to transmit at least one ultrasound pressure wave along a new first lateral axial ray laterally displaced from the new principal axial ray; and transmit beam forming to transmit at least one ultrasound pressure wave along a new second lateral axial ray laterally displaced from the new principal axial ray and the new first lateral axial ray.

9. The method of claim 7, further comprising:

transmit beam forming to transmit at least one ultrasound pressure wave along a new principal axial ray different from the initial principal axial array;

transmit beam forming to transmit at least one ultrasound pressure wave along a new first lateral axial ray laterally displaced from the new principal axial ray; and transmit beam forming to transmit at least one ultrasound pressure wave along a new second lateral axial ray laterally displaced from the new principal axial ray and the new first lateral axial ray.

10. The method of claim 1 wherein generating a first number of ultrasound pressure waves includes transmit beam forming to transmit the ultrasound pressure waves along at least three axial rays, the three axial rays laterally spaced from one another.

11. The method of claim 1 wherein receiving a first number of ultrasound return signals from a principal sample volume and at least one additional sample volume includes:

receive beam forming to receive ultrasound return signals in response to the at least one ultrasound pressure wave transmitted along an initial principal axial ray;

receive beam forming to receive ultrasound return signals in response to the at least one ultrasound pressure wave transmitted along an initial first lateral axial ray; and receive beam forming to receive ultrasound return signals in response to the at least one ultrasound pressure wave along an initial second lateral axial ray.

12. The method of claim 1 wherein determining at least one characteristic of the return signals in the principal sample volume and the at least one additional sample volume includes evaluating at least one value indicative of at least one of a power, a variance, a velocity, of a set of echo data.

13. The method of claim 12 wherein selecting a new principle sample volume includes:

selecting a new principal sample volume to at least partially coincide with a region of interest in an object being imaged; and selecting a number of additional sample volumes to be sampled that have at least respective portions thereof that are at least one of axially displaced or laterally displaced with respect to the new principal sample volume.

14. The method of claim 12 wherein selecting a new principle sample volume includes:

selecting a new principal sample volume to be centered with respect to at least one structure of an object being imaged; and selecting a number of additional sample volumes to be sampled that have at least respective portions thereof that are at least one of axially displaced or laterally displaced with respect to the new principal sample volume.

15. An ultrasound imaging system, comprising:

at least one transducer array;

at least one control system including a number of beam formers communicatively coupled to the at least one transducer array and at least one controller communicatively coupled to the beam formers, the control system configured to:

generate a number of ultrasound pressure waves by the at least one transducer array;

receive a number of ultrasound return signals via the at least one transducer array, the number of ultrasound return signals received from a principal sample volume and at least one additional sample volume that is axially or laterally displaced with respect to the principal sample volume;

determine a characteristic of the return signals in the principal sample volume and at least one additional sample volume; and select a new principal sample volume location based at least in part on the determined characteristic of the return signals in the principal sample volume or the at least one additional sample volume; and at least one display communicatively coupled to the control system to receive at least image data therefrom for display of images on the display.

16. The ultrasound imaging system of claim 15 wherein, the control circuit is configured to:

select a number of additional sample volumes to be sampled that have at least respective portions thereof that are at least one of axially displaced or laterally displaced with respect to the new principal sample volume.

17. The ultrasound imaging system of claim 16 wherein the control circuit is further configured to:

generate a second number of ultrasound pressure waves directed to the new principal sample volume and at least one of the additional sample volumes.

18. The ultrasound imaging system of claim 15 wherein the control circuit is configured to:

select at least two additional sample volumes to be sampled that have at least respective portions thereof that are laterally opposed to one another across the new principal sample volume.

19. The ultrasound imaging system of claim 15 wherein the control circuit is configured to:

select an additional sample volume as a new principal sample volume; and select at least two additional sample volumes to be sampled that have at least respective portions thereof that are axially opposed to one another across the new principal sample volume.

20. The ultrasound imaging system of claim 15 wherein to generate a number of ultrasound pressure waves, the control circuit:

generates at least one ultrasound pressure wave along an initial principal axial ray;

generates at least one ultrasound pressure wave along an initial first lateral axial ray laterally displaced from the initial principal axial ray; and generates at least one ultrasound pressure wave along an initial second lateral axial ray laterally displaced from the initial principal axial ray and the initial first lateral axial ray.

21. The ultrasound imaging system of claim 20 wherein the control circuit is further configured to:

generate at least one ultrasound pressure wave along a new principal axial ray;

generate at least one ultrasound pressure wave along a new first lateral axial ray laterally displaced from the new principal axial ray; and generate at least one ultrasound pressure wave along a new second lateral axial ray laterally displaced from the new principal axial ray and the new first lateral axial.

22. The ultrasound imaging system of claim 20 wherein the control circuit is further configured to:
- generate at least one ultrasound pressure wave along a new principal axial ray different from the initial principal axial array;
- generate at least one ultrasound pressure wave along a new first lateral axial ray laterally displaced from the new principal axial ray; and
- generate at least one ultrasound pressure wave along a new second lateral axial ray laterally displaced from the new principal axial ray and the new first lateral axial ray.

23. The ultrasound imaging system of claim 15 wherein the control circuit is further configured to determine the characteristic of the return signals in the principal sample volume and the at least one additional sample volume by:
- evaluating at least one value indicative of at least one of a power, a variance, a velocity, in the received ultrasound return signals.

24. The ultrasound imaging system of claim 23 wherein, the control circuit is configured to:
- select a new principal sample volume to be sampled to at least partially coincide with a region of interest in an object being imaged; and
- select a number of additional sample volumes to be sampled that have at least respective portions thereof that are axially or laterally displaced with respect to the new principal sample volume.

25. The ultrasound imaging system of claim 23 wherein the control circuit is configured to:
- select a new principal sample volume to be sampled to be centered with respect to at least one structure of an object being imaged; and
- select a number of additional sample volumes to be sampled that have at least respective portions thereof that are axially or laterally displaced with respect to the new principal sample volume.

* * * * *